United States Patent
Mittiga

Patent Number: 5,819,765
Date of Patent: Oct. 13, 1998

[54] FINGER GLOVE COMPRISING AREAS PREPARED FOR ORAL HYGIENE

[76] Inventor: Maria Ida Mittiga, Via Bartolomeo Intieri 3, 00191 Roma, Italy

[21] Appl. No.: 737,231
[22] PCT Filed: Jun. 14, 1994
[86] PCT No.: PCT/IT94/00085
  § 371 Date: Nov. 8, 1996
  § 102(e) Date: Nov. 8, 1996
[87] PCT Pub. No.: WO95/31154
  PCT Pub. Date: Nov. 23, 1995

[30] Foreign Application Priority Data

May 11, 1994 [IT] Italy ................................ MI94A0933

[51] Int. Cl.$^6$ ........................ A45D 44/18; A46B 5/04
[52] U.S. Cl. ....................... 132/309; 15/227; 206/63.5
[58] Field of Search ............................... 132/308, 309; 15/110, 167.1, 227; 206/368, 369, 63.5

[56] References Cited

U.S. PATENT DOCUMENTS

| | | |
|---|---|---|
| 3,298,507 | 1/1967 | Micciche ................................... 15/227 |
| 3,608,566 | 9/1971 | Storandt ................................... 132/209 |
| 3,902,509 | 9/1975 | Tundermann et al. .................... 15/277 |
| 4,292,705 | 10/1981 | Stouffer ................................... 132/308 |
| 4,617,694 | 10/1986 | Bori ....................................... 132/308 |
| 4,972,946 | 11/1990 | Whittaker ............................... 206/368 |
| 5,068,941 | 12/1991 | Dunn ....................................... 15/227 |
| 5,213,428 | 5/1993 | Salman .................................... 15/227 |
| 5,228,433 | 7/1993 | Rosen .................................... 206/369 |
| 5,348,153 | 9/1994 | Cole ...................................... 206/63.5 |
| 5,487,201 | 1/1996 | Hansen et al. ......................... 132/309 |

FOREIGN PATENT DOCUMENTS

| | | | |
|---|---|---|---|
| 3517094 | 11/1986 | Germany ................................. 15/227 |
| 2144032 | 2/1985 | United Kingdom ..................... 15/227 |

Primary Examiner—Todd E. Manahan
Attorney, Agent, or Firm—Michael J. Striker

[57] ABSTRACT

An appliance for hygiene and care of an oral cavity has a thin rubber glove for one finger of a hand, the glove having at least one operative surface area extending to an end of said glove so as to correspond to a position of a finger tip, and a sealed hollow member provided in the at least one operative surface area and accommodating an active product, the sealed hollow member being formed so that during rubbing of said at least one operative surface area against teeth or gums the active product emerges from the sealed hollow member and is spread over the teeth and gums.

20 Claims, 4 Drawing Sheets

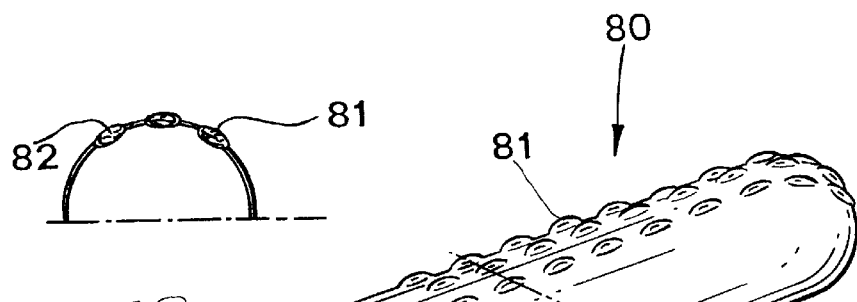
fig. 4B
fig. 4A
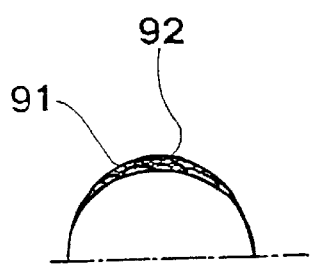
fig. 5B
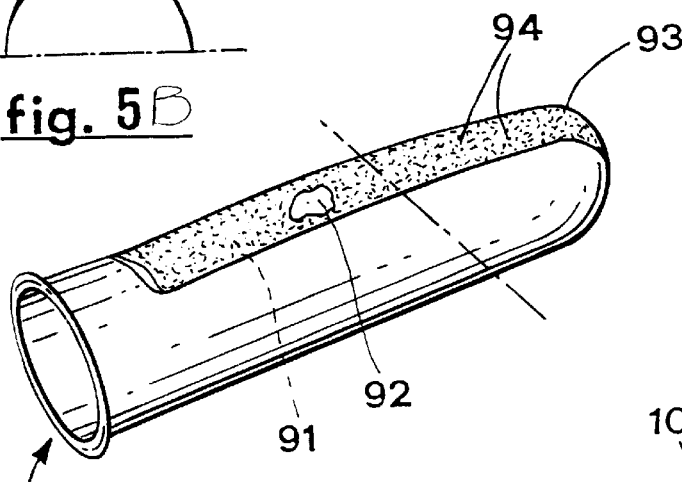
fig. 5A
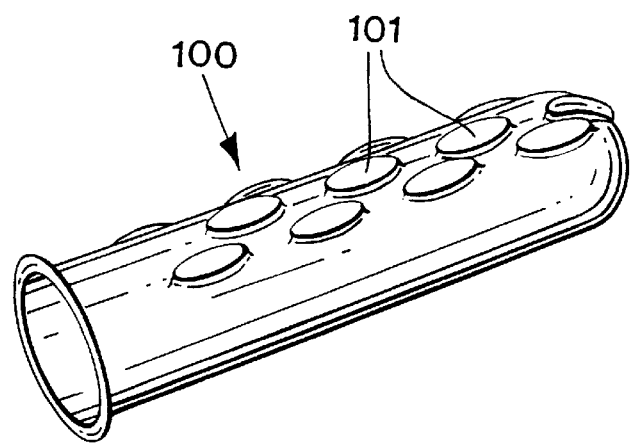
fig. 6

FINGER GLOVE COMPRISING AREAS PREPARED FOR ORAL HYGIENE

BACKGROUND OF THE INVENTION

The present invention relates to appliances and means for keeping the teeth clean.

Oral hygiene for preventing disorders of the teeth and surrounding gum tissues, disorders which may even become series and incurable, is known to be of great importance for general health.

Lack of oral hygiene leads to the spread of harmful germs, among the various species of micros present in the mucous, producing film and causing diseases, especially toothed decay mainly due to the presence of streptoccus mutans. The film that forms on the teeth reappears five hours after removal and can turn into brown tartar caused by calcification of the bacteria and other substances it contains, which in turn further assist accumulation of film leading to irritation and shrinkage of the gums. Food, especially when too soft leaves residual matter between the teeth where germs find a suitable breeding ground. Residual sugar creates an acid damaging for tooth enamel.

In order to prevent mouth diseases, proper oral hygiene is therefore a necessity. At present it is performed by a toothbrush on a handle, which must be used for at least three minutes after each meal. In this case however the finger act on the teeth through two intermediate elements: The handle of the toothbrush and the bristles. These intermediate elements clearly impede any real perception during cleaning, since reactions by the teeth can not be felt by the fingers. Since it is difficult if not impossible to see inside the mouth during tooth cleaning, the presents methods of oral hygiene must necessarily rough and ready and prevent any possibility of proper check of the results. By the very nature, bristles are a hot bead of bacteria and of germs that collect among the teeth. Rinsing the toothbrush under a rinsing after use is almost entirely ineffective, since the water can not penetrate between the toughs of bristles and even less among the bristles themselves. Action by toothbrushes may even be negative if used by the members of a family and exchanged indiscriminately among them. The idea of a disposable toothbrush to be discarded after use is unthinkable, since the construction of an efficient disposable toothbrush is complex and therefore to costly.

German patent document DE-A-3232313 discloses a glove of rubber and the like for the finger of a hand, that comprises an active area with tufts of bristles or a series of small rubber nodules or depressions filled with dentifrice or medicinal paste. The glove can assist in cleaning and massaging the teeth and gums and exert a beneficial action both for hygiene and general care. However, its effectiveness is limited especially because of the small quantity of active product, such as dentifrice or medicament that is applied to the teeth from the active area.

SUMMARY OF THE INVENTION

Accordingly, it is a purpose of the present invention to provide an improvement in cleaning the teeth and gums and an application of health-enhancing products, and also to offer increased protection against bacterial perforation with means whose cost is practically negligible as will be explained hereinbelow.

In accordance with the invention an appliance includes a very fine natural or synthetic rubber glove for one finger of the hand, whose surface has one or more specially prepared operational areas extending longitudinally to the tip and particularly including the finger tip. Since this area is situated on the inside of the finger, the appliance can rub it against the teeth, gums and elsewhere in the oil cavity, assisted by dentifrice and other products for cleaning the teeth, tonifying the gums, massaging and applying beneficial action generally.

One of the products can advantageously contain fluorine to keep the teeth in good conditions, and can also remove a film. The products can be applied dry or in liquid form, with or without water.

The operational areas can be formed as a longitudinal strip, while other operational areas can be shaped variously, for example polygonal or discoid.

In accordance with one embodiment of the invention, the operational areas are formed as sealed cells containing an active product in form so that the cell walls on the outside surface of the finger glove are very thin or made so as to break open during massaging the teeth and gums.

The above mentioned areas can be the same or different, associated or single, laid side-by-side or otherwise placed. The active product can be dentifrice, detergent or another beneficial substance. It can be a fluid, a powder, or a relief-providing product, such as a painkiller, etc.

Maximum hygiene is assured since the appliance can be disposed of after use because of its very low cost.

When the appliance is designed in accordance with the present invention, it permits highly effective safe and sensitive care of the oral cavity both in cleaning the teeth and in application of medicinal substances.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4a is a perspective view of the glove provided with closed cells which are filled with an active fluid;

FIG. 4b is a view showing the individual closed cell filled with the active fluid;

FIG. 5a is an active view of the glove provided with a flat oblong chamber filled with the active fluid and having minute perforations on the external surface;

FIG. 5b is a view showing the flat oblong chamber filled with the active fluid;

FIG. 6 is a perspective view of the glove having a circular active area;

DESCRIPTION OF PREFERRED EMBODIMENTS

Figure 1:
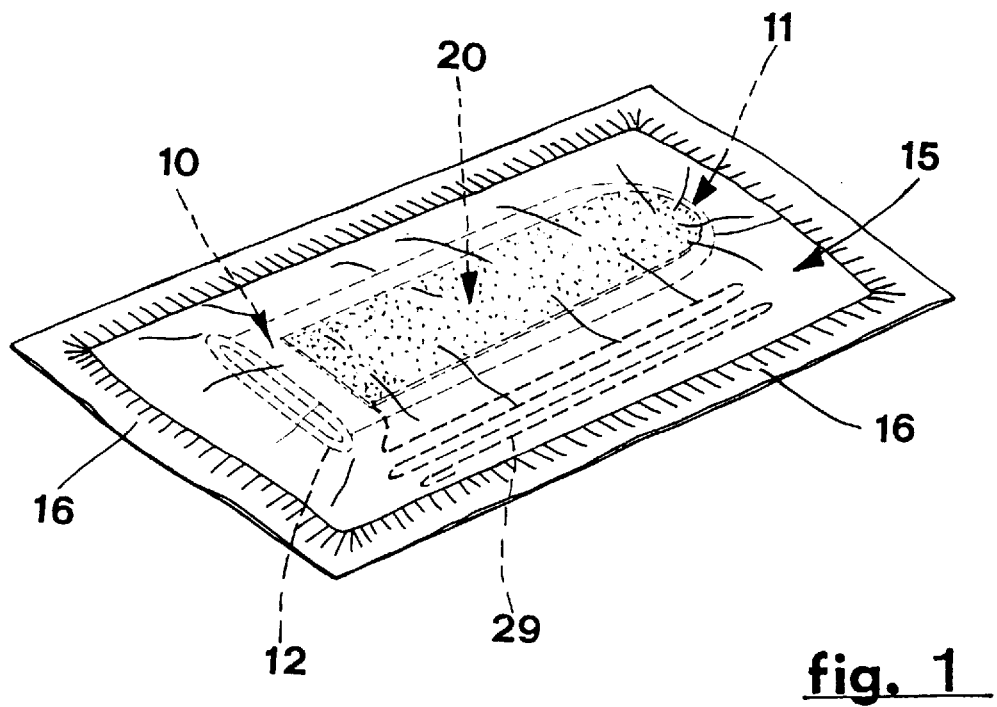
FIG. 1 is a view showing an appliance formed as a finger glove in accordance with the present invention and protected by a sealed waterproof packet.

A glove 10 in accordance with the present invention has a substantially cylindrical shape for a finger of a hand. It is composed of fine flexible natural or synthetic rubber and has a rounded tip 11 and a thickened edge 12 at an open end. An active longitudinal strip 20 is fixed on the glove and extends from the tip to a short distance from the base. Its width corresponds substantially to a half the gloves circumference. The size of the glove substantially corresponds to the size of a middle finger of an adult person. The glove is protected by a packet 15 of a waterproof material sealed all around its edges 16, as shown in FIG. 1.

Figure 2:
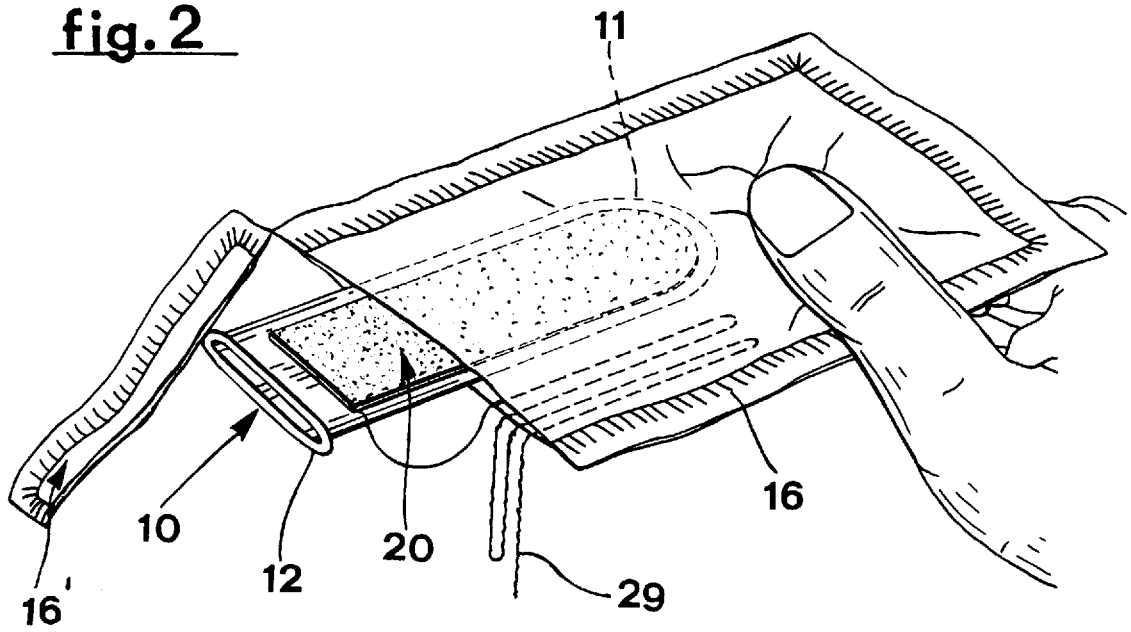
FIG. 2 is a perspective view of the inventive glove outside of the packet.
Figure 3:
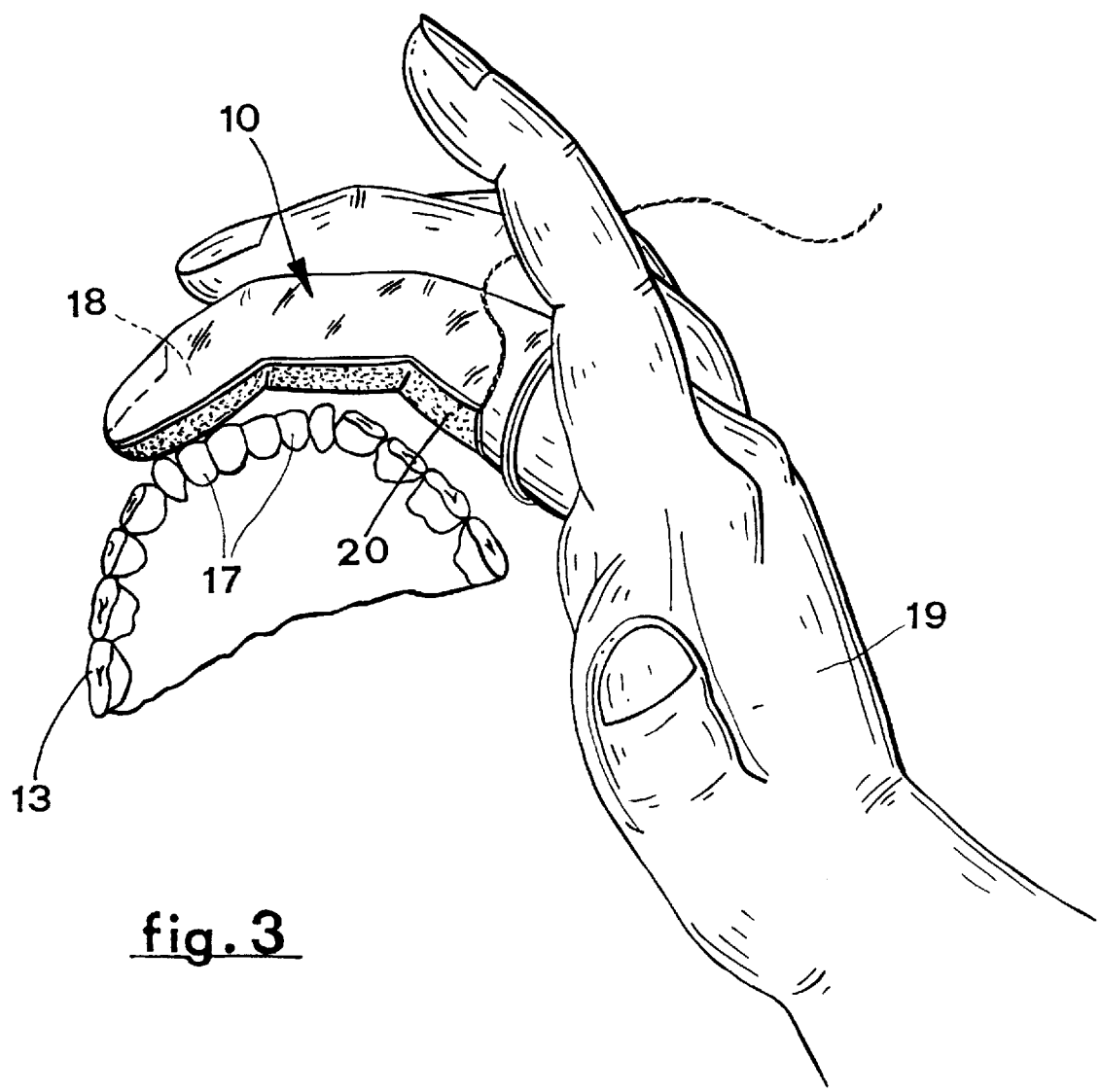
FIG. 3 is a perspective view of the glove worn on a middle finger of a user while cleaning the teeth.

In order to use the glove, one end 16' is torn off the packet, the glove is taken out and fitted onto the middle finger 18 of the hand 19, so that the active strip 20 lies on the inner side of the finger 18, as shown in FIG. 2. Therefore great effectiveness is assured by the use of a finger to reach all parts of the mouth and of the teeth 17 with maximum sensitivity, and thereby with an action that is both thorough and gentle, as shown in FIG. 3.

As shown in FIGS. 4a and 4b, the cylindrical surface of a finger glove 80 carries a plurality of closed cells 81 which contain an active fluid 82 for the teeth. When the glove is rubbed against the teeth, the cells break open and spread the fluid all over the teeth or on the gums as well. Therefore it does the work of an ordinary toothbrush or other means for treating the oral cavity.

In accordance with an embodiment shown in FIGS. 5a and 5b, a finger glove 90 has a closed oblong chamber 91 which is filled with fluid 92. Its surface 93 is perforated with minute holes 94. Unless pressure is exerted on the chamber, the fluid remains inside it. However, when the chamber is rubbed against the teeth, the internal pressure causes the fluid to seep out through the holes onto the teeth or onto the other parts of the mouth.

In the embodiment shown in FIG. 6, the finger glove 100, has, instead of the active rectangular strips, active circular raised areas 101 The raised areas 101 are placed near one another as described hereinabove, but their shapes are different. The circular shape can be also replaced by other shapes, such as an oval shape, a polygonal shape, and another shape.

Figure 7:
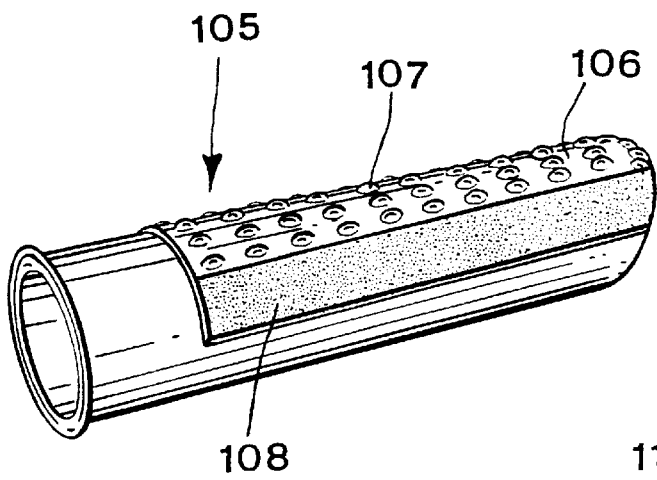
FIG. 7 is a perspective view of the glove having two active strips of a different type arranged one along the other.

In the embodiment shown in FIG. 7 the finger glove 105 has two rectangular longitudinal strips which are placed side-by-side with one another. The strip 106 has protuberances 107, while the strip 108 is composed of thick absorbent paper with a rough surface.

Figure 8:
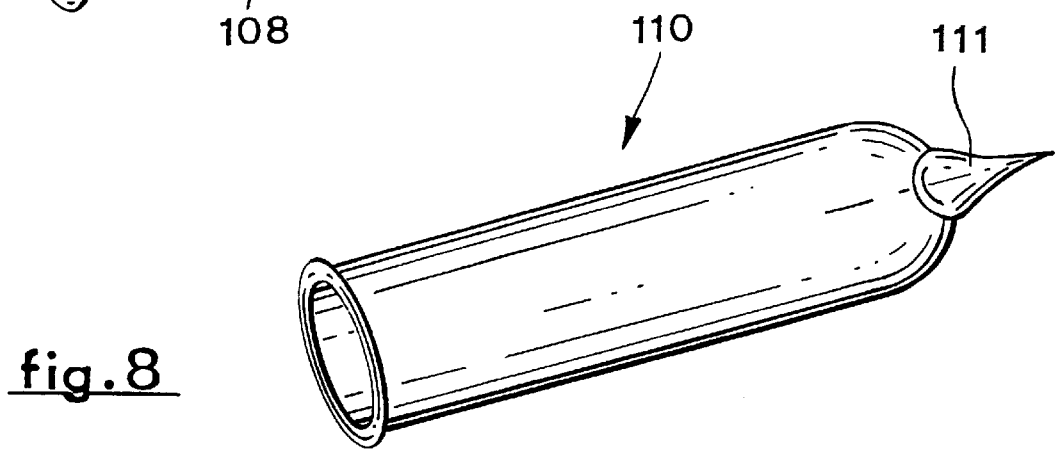
FIGS. 8–10 are perspective views of the glove with soft tapering tips extending in an axial, lateral and oblique direction correspondingly.
Figure 9:
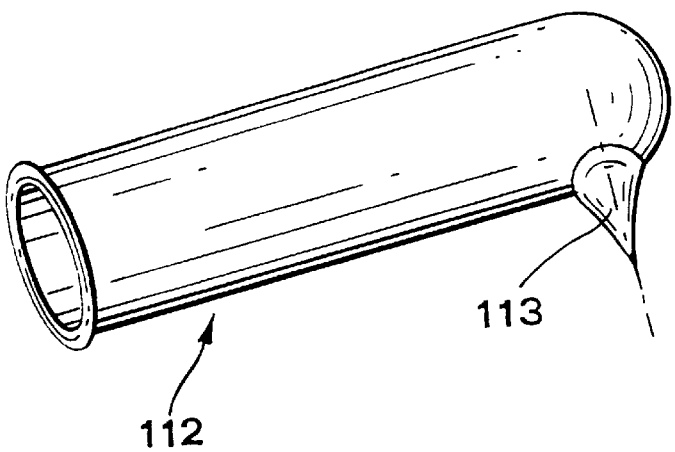
Figure 10:
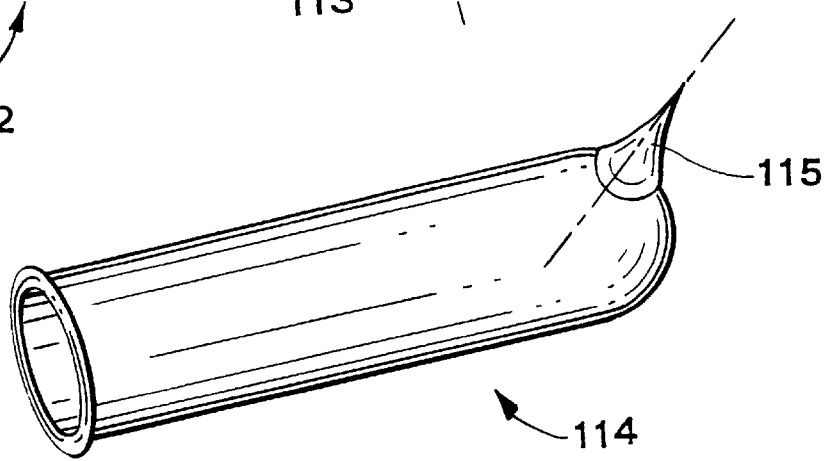

Finally, FIGS. 8, 9 and 10 show finger gloves 110, 112, 114 provided with soft tapering projections 111, 113, 115. The projections extend axially, laterally, or obliquely correspondingly, for applying action in the oral cavity. These projections can be added to all the finger gloves described hereinabove.

The finger glove 10 can also have a thread of a dental floss 29 which is attached to it. Therefore, it is very useful for removing film between the teeth.

I claim:

1. An appliance for hygiene and care of an oral cavity, comprising a thin rubber glove for one finger of a hand, said glove having at least one operative surface area extending to an end of said glove so as to correspond to a position of a finger tip; and a sealed hollow member provided in said at least one operative surface area and accommodating an active product, said sealed hollow member being formed so that during rubbing of said at least one operative surface area against teeth or gums said active product emerges from said sealed hollow member and is spread over the teeth and gums.

2. An appliance as defined in claim 1, wherein said glove is composed of natural rubber.

3. An appliance as defined in claim 1, wherein said glove is composed of synthetic rubber.

4. An appliance as defined in claim 1, wherein said sealed hollow member is formed as a cell which brakes during rubbing against the teeth or gums.

5. An appliance as defined in claim 1, wherein said sealed hollow member is formed by a plurality of cells which brake during rubbing of the teeth and gums.

6. An appliance as defined in claim 1, wherein said sealed hollow member is formed as a flat sealed chamber with a surface containing a plurality of openings through which the active product seeps during rubbing against the teeth or gums.

7. An appliance as defined in claim 1, wherein said glove has a plurality of said operative surface areas which are formed differently from one another.

8. An appliance as defined in claim 1, wherein said glove has a plurality of said operative surface areas which are identical to one another.

9. An appliance as defined in claim 1, wherein said at least one operative surface area is formed as a longitudinal strip.

10. An appliance as defined in claim 1, wherein said at least one operative surface area has a polygonal shape.

11. An appliance as defined in claim 1, wherein said at least one operative surface area has a discoid shape.

12. An appliance as defined in claim 1, and further comprising a sealed water proof packet which encloses said glove.

13. An appliance as defined in claim 12, wherein said packet contains a product beneficial to an oral cavity.

14. An appliance as defined in claim 12, wherein an inside of said packet and also said glove are sterile.

15. An appliance as defined in claim 1, and further comprising a thread formed as a dental floss and attached to said glove.

16. An appliance as defined in claim 1, wherein said active product contains fluorine.

17. An appliance as defined in claim 1, wherein said glove has a closed rounded end with a soft pointed tapered head facilitating mechanical action in an oral cavity.

18. An appliance as defined in claim 17, wherein said tapered head is arranged axially relative to said glove.

19. An appliance as defined in claim 17, wherein said tapered head is arranged laterally to said glove.

20. An appliance as defined in claim 17, wherein said tapered head is arranged obliquely to said glove.

* * * * *